(12) United States Patent
Lee

(10) Patent No.: US 11,344,099 B2
(45) Date of Patent: May 31, 2022

(54) DROPPER TYPE COSMETIC CONTAINER

(71) Applicants: PUM-TECH KOREA CO., LTD, Incheon (KR); F.S KOREA INDUSTRIES INC, Seoul (KR)

(72) Inventor: Do Hoon Lee, Incheon (KR)

(73) Assignees: PUM-TECH KOREA CO., LTD., Incheon (KR); F.S KOREA INDUSTRIES INC, Seoul (KR)

( * ) Notice: Subject to any disclaimer, the term of this patent is extended or adjusted under 35 U.S.C. 154(b) by 0 days.

(21) Appl. No.: 17/195,355

(22) Filed: Mar. 8, 2021

(65) Prior Publication Data

US 2022/0133014 A1 May 5, 2022

(30) Foreign Application Priority Data

Nov. 5, 2020 (KR) .................... 10-2020-0146692

(51) Int. Cl.
| | |
|---|---|
| A45D 34/04 | (2006.01) |
| B65D 47/18 | (2006.01) |
| A61M 35/00 | (2006.01) |
| B01L 3/02 | (2006.01) |

(52) U.S. Cl.
CPC ............. *A45D 34/04* (2013.01); *A61M 35/00* (2013.01); *B01L 3/0282* (2013.01); *B65D 47/18* (2013.01)

(58) Field of Classification Search
CPC .... A45D 34/04; A45D 34/043; A45D 34/045; A61M 35/00; A61M 35/003; B01L 3/0282; B65D 47/18
USPC ........................ 222/420–422; 401/188 R, 127
See application file for complete search history.

(56) References Cited

U.S. PATENT DOCUMENTS

| | | | | |
|---|---|---|---|---|
| 8,403,008 B2 * | 3/2013 | Bouix | ................... | G01F 11/025 141/23 |
| 9,078,507 B2 * | 7/2015 | Lee | ........................ | A45D 34/00 |
| 9,089,868 B2 * | 7/2015 | Lee | ........................ | B05B 11/309 |
| 9,234,781 B2 * | 1/2016 | Lee | ........................ | B65D 41/56 |
| 9,546,026 B2 * | 1/2017 | Drugeon | ............... | B01L 3/0282 |
| 9,609,935 B2 * | 4/2017 | Lee | ..................... | B05B 11/3001 |

(Continued)

FOREIGN PATENT DOCUMENTS

KR      20-0463676 Y     11/2012

*Primary Examiner* — Paul R Durand
*Assistant Examiner* — Randall A Gruby
(74) *Attorney, Agent, or Firm* — Heedong Chae; Lucem, PC

(57) ABSTRACT

Disclosed is a dropper type cosmetic container. The dropper type cosmetic container includes a container body for containing a cosmetic material therein; a fixing member fixedly coupled to the container body and formed with a cylinder; an elevating member coupled to the fixing member to move up or down and formed with a synthetic resin elastic body; a dropper tube connected to the fixing member to suck and discharge the cosmetic material contained in the container body; a rotating member rotatably coupled to the fixing member; and a push button moving up or down together with the elevating member and having one side coupled to a piston, wherein a movement limiting protrusion is formed on one side of the elevating member, and a movement limiting hole is formed in one side of the push button, so that the movement limiting protrusion is coupled to the movement limiting hole, thereby limiting a movement section of the push button and a compression range of the elastic body.

10 Claims, 7 Drawing Sheets

(56) References Cited

U.S. PATENT DOCUMENTS

| | | | |
|---|---|---|---|
| 10,875,688 B1* | 12/2020 | Hawry | B65D 47/20 |
| 11,235,915 B2* | 2/2022 | Kim | B65D 47/18 |
| 2013/0074983 A1* | 3/2013 | Choi | A45D 34/00 |
| | | | 141/23 |
| 2014/0020789 A1* | 1/2014 | Duquet | B65D 47/18 |
| | | | 141/24 |
| 2016/0368634 A1* | 12/2016 | Lee | A45D 34/00 |
| 2017/0082475 A1* | 3/2017 | Ham | B05B 11/02 |
| 2021/0229879 A1* | 7/2021 | Choi | A45D 40/26 |

* cited by examiner

DROPPER TYPE COSMETIC CONTAINER

CROSS-REFERENCE TO RELATED APPLICATIONS

This application claims the priority of Korean Patent Application No. 10-2020-0146692 filed on Nov. 5, 2020, in the Korean Intellectual Property Office, the disclosure of which is incorporated herein by reference.

BACKGROUND

One aspect of the present disclosure relates to a dropper type cosmetic container, and more particularly, to a dropper type cosmetic container in which the compression range of an elastic body elastically supporting a push button is constantly adjusted by limiting a moving section of the push button, so that the elastic body is prevented from being damaged and deformed, thereby smoothly performing the discharge operation of a cosmetic material even if repeatedly used.

Cosmetics refer to articles used on the human body to clean and beautify the human body, thereby adding attractiveness, changing appearance, or maintaining or promoting the health of skin or hair.

Such cosmetics are largely divided into basic cosmetics, functional cosmetics and color cosmetics according to the purpose of use.

The functional cosmetics refer to cosmetics used to help whitening the skin or improve wrinkles of the skin and protect the skin from ultraviolet rays.

However, since most of the functional cosmetics described above are very expensive, it is economical to supply and use the cosmetic contents in an exact quantity to the area where the cosmetic is applied. In the case of taking the cosmetic contents on the palm of a hand for use as in the related art, since the amount of the cosmetic contents absorbed in the palm is large, expensive cosmetic contents are wasted.

In addition, since the functional cosmetics do not use preservatives, the cosmetic contents are very susceptible to contamination. When the cosmetic contents are used by sticking the contents on a hand as in conventional cream-type cosmetics, or by discharging the cosmetic contents by touching the opening of the container with the palm as in lotion, the contaminants of the hand penetrate into the cosmetic container body, thereby causing the cosmetic contents to deteriorate.

Accordingly, when using functional cosmetics, it is preferable to use a quantitative amount. When too much or less cosmetics are used, it may cause side effects or have no effect on the skin. Therefore, there is a need to provide a cosmetic container capable of quantitatively extracting the contents.

In order to solve the problems, there has been developed a dropper type cosmetic container which allows the user to suck the cosmetic contents with a dropper and then discharge the cosmetic material to the skin where the cosmetic is applied.

Therefore, there is a need to develop a cream-type cosmetic container which can store different contents in two or more separated spaces, has no restriction on the type of stored cosmetics, is hygienic, and can be used conveniently.

The conventional dropper type cosmetic container described above includes a cylinder inside a container lid, a piston that moves up and down by the elasticity of a spring in the cylinder, and a button that is formed on the upper side of the piston, so that the cosmetic contents in a container body are discharged to the outside by the operation of the button.

However, according to the conventional dropper type cosmetic container, whenever cosmetic contents are used, there is an inconvenience of sucking the cosmetic contents by pressing a button after opening the container lid. In addition, since the amount of cosmetic contents sucked through the dropper tube is different each time depending on the degree of pressing the button by the user, it is difficult to discharge a certain amount each time.

To solve the above-described problem, there has been disclosed a dropper type cosmetic container in Korean Registered Utility Model No. 20-0463676. In the related art, when a cap part is coupled to a container body, a retractable button moved down is moved upwardly in the process of separating the cap part from the container body by rotating the cap part, and at the same time, a piston rod and a piston support part are moved in the same direction to make cosmetics into the dropper tube, thereby sucking the cosmetic material into the dropper tube and discharging the cosmetic material to an outside. Therefore, it is possible to quantitatively extract cosmetics and to improve convenience in use.

However, according to the related art, since the elastic member providing elasticity to the retractable button is formed of a metallic spring, the elastic member of the metallic spring must be separated from other parts and disposed of for recycling of the container. For this reason, recycling is not easy.

Thus, even though the elastic member is formed of a synthetic resin material, the retractable button is contained inside the cap part in a state in which the elastic member is compressed, so that the resilience of the elastic member is deteriorated due to the material properties of the synthetic resin during long-term use. When the retractable button protruding to the outside of the cap is pressed to the maximum, the elastic member is excessively compressed and the elastic member is damaged, or when the elastic member is repeatedly used, the elastic member is deformed, so that the operation of discharging a cosmetic material is not performed smoothly.

SUMMARY

To solve the problems described above, an object of the present disclosure is to provide a dropper type cosmetic container that can constantly adjust the compression range of a synthetic resin elastic body that elastically supports a push button by restricting the movement section of the push button, thereby preventing the detachment of the push button and preventing damage and deformation due to excessive compression of the synthetic resin elastic body. In addition, as the restoring force of the synthetic resin material elastic body is always properly maintained, even if the dropper type cosmetic container is repeatedly used, a cosmetic discharge operation can be performed smoothly.

Another object of the present disclosure is to provide a dropper type cosmetic container in which an elastic body for elastically supporting the push button is formed of a synthetic resin material in the same manner as other parts, so that the elasticity and repulsion force are not lowered compared to a conventional metallic elastic body, and the elastic body is easily separated and collected or recycling is easy.

Still another object of the present disclosure is to provide a dropper type cosmetic container in which a push button is inserted into a cap, stored, and then protruded and pressed to the outside of the cap by the operation of the cap, and a synthetic resin elastic body that elastically supports the push button is maintained in an uncompressed state while being elevated together with the push button, so that it is possible to prevent the restoring force of the synthetic resin elastic body from deteriorating.

According to one aspect of the present disclosure, there is provided a dropper type cosmetic container which includes a container body for containing a cosmetic material therein; a fixing member fixedly coupled to the container body and formed with a cylinder; an elevating member coupled to the fixing member to move up or down and formed with a synthetic resin elastic body; a dropper tube connected to the fixing member to suck and discharge the cosmetic material contained in the container body; a rotating member rotatably coupled to the fixing member; and a push button moving up or down together with the elevating member and having one side coupled to a piston, wherein a movement limiting protrusion is formed on one side of the elevating member, and a movement limiting hole is formed in one side of the push button, so that the movement limiting protrusion is coupled to the movement limiting hole, thereby limiting a movement section of the push button and a compression range of the elastic body.

The container body may be formed with an inlet portion, and the inlet portion is formed with a wiper which is in close contact with an outer periphery of the dropper tube.

The fixing member may be formed with a vertical guide hole, and the elevating member may be formed on an inner periphery thereof with a vertical guide protrusion so that the vertical guide protrusion is coupled to the vertical guide hole.

The dropper tube may have one side formed with a suction/discharge port and an opposite side connected to an inside of the cylinder of the fixing member.

The elevating member may include an elevating body surrounding an upper outer side of the fixing member and an elastic body formed on one side of the elevating body to elastically support the push button.

The elevating body and the elastic body of the elevating member may be integrally injection-molded.

The rotating member may include a rotation inner cap and a rotation outer cap, and the rotation inner cap and the rotation outer cap may be formed with a fitting protrusion and a fitting groove, respectively, so that the rotation inner cap and the rotation outer cap are coupled to each other.

The rotating member and the elevating member may be formed with an elevating protrusion and an elevating guide hole, respectively, so that the rotating member and the elevating member are coupled to each other.

The push button may have a protrusion extending to one side to surround an outer periphery of the elevating member, and the protrusion may be formed with a movement limiting hole that extends linearly.

The elevating member including the elastic body and the push button including the piston may move up or down together as a single module when the rotating member rotates, and the elastic body may be always maintained in an uncompressed state.

According to the embodiments of the present disclosure, the compression range of the synthetic resin elastic body that elastically supports a push button by restricting the movement section of the push button may be constantly adjust, thereby preventing the detachment of the push button and preventing damage and deformation due to excessive compression of the synthetic resin elastic body. In addition, as the restoring force of the synthetic resin material elastic body is always properly maintained, even if the dropper type cosmetic container is repeatedly used, a cosmetic discharge operation may be performed smoothly.

According to the embodiments of the present disclosure, the elastic body for elastically supporting the push button is formed of the synthetic resin material in the same manner as other parts, so that the elasticity and repulsion force may not be lowered compared to a conventional metallic elastic body, and the elastic body may be easily separated and collected or recycling may be easy.

According to the embodiments of the present disclosure, the push button may be inserted into the cap, stored, and then protruded and pressed to the outside of the cap by the operation of the cap, and a synthetic resin elastic body that elastically supports the push button may be maintained in an uncompressed state while being elevated together with the push button, so that it is possible to prevent the restoring force of the synthetic resin elastic body from deteriorating.

DETAILED DESCRIPTION OF THE EMBODIMENTS

Figure 1:
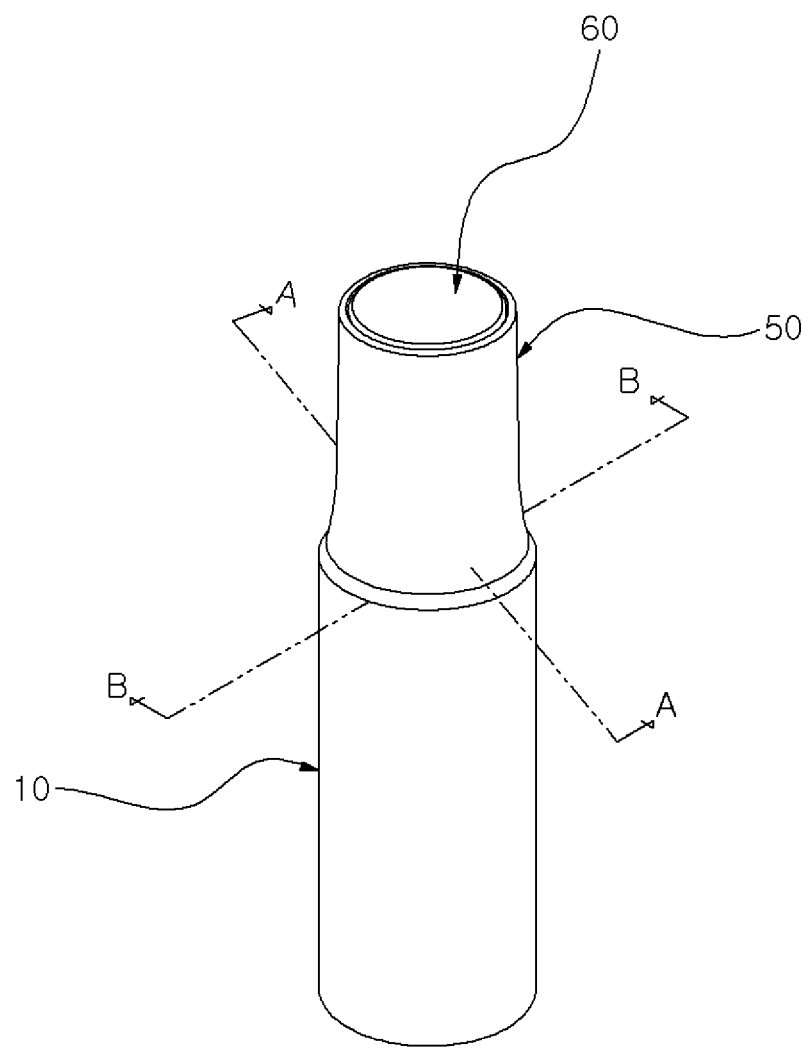
FIG. 1 is a perspective view of a cosmetic container according to an embodiment of the present disclosure.

In the following detailed description, reference is made to the accompanying drawings that show, by way of illustration, specific embodiments in which the inventive concept may be practiced. These embodiments are described in sufficient detail to enable those skilled in the art to practice the inventive concept. It is to be understood that the various embodiments of the inventive concept, although different, are not necessarily mutually exclusive. For example, a particular feature, structure, or characteristic described herein in connection with one embodiment may be implemented within other embodiments without departing from the spirit and scope of the inventive concept. In addition, it is to be understood that the location or arrangement of individual elements within each disclosed embodiment may be modified without departing from the spirit and scope of the inventive concept.

The following detailed description is, therefore, not to be taken in a limiting sense, and the scope of the inventive concept is defined only by the appended claims, appropriately interpreted, along with the full range of equivalents to which the claims are entitled. In the drawings, like numerals refer to the same or similar functionality throughout the several views.

With respect to the terms used in an example embodiment of the disclosure, general terms currently and widely used are selected in view of function with respect to the disclosure. However, the terms may vary according to an intention of a technician practicing in the pertinent art, an advent of new technology, etc. In specific cases, terms may be chosen arbitrarily, and in this case, definitions thereof will be described in the description of the corresponding disclosure. Accordingly, the terms used in the description should not necessarily be construed as simple names of the terms, but be defined based on meanings of the terms and overall contents of the present disclosure.

In the present disclosure, when some part 'includes' some elements, unless explicitly described to the contrary, it means that other elements may be further included but not excluded.

Hereinafter, a dropper-type cosmetic container according to an embodiment of the present disclosure will be described in detail with reference to the accompanying drawings.

Figure 2:
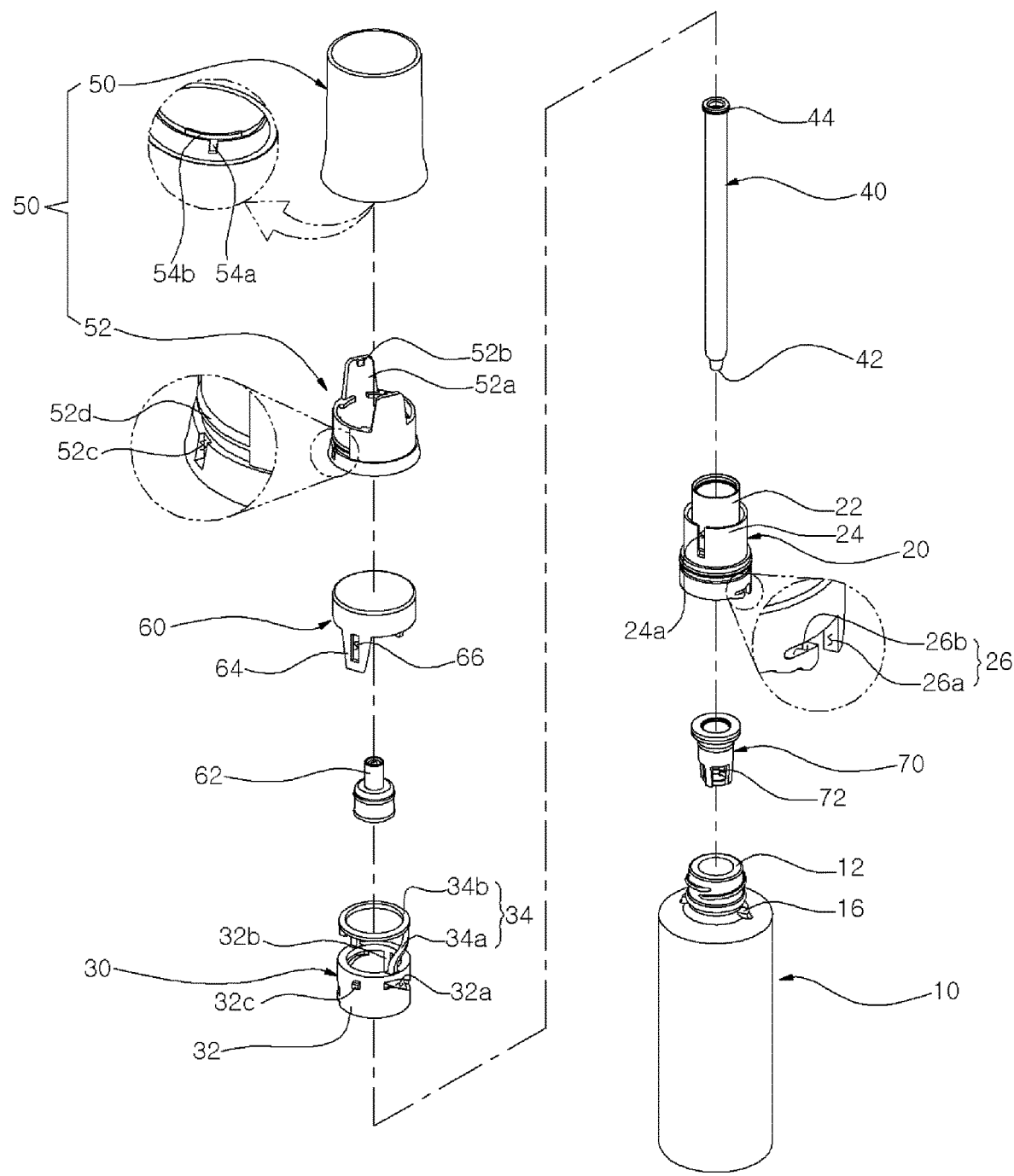
FIG. 2 is an exploded perspective view of a cosmetic container according to an embodiment of the present disclosure.
Figure 3:
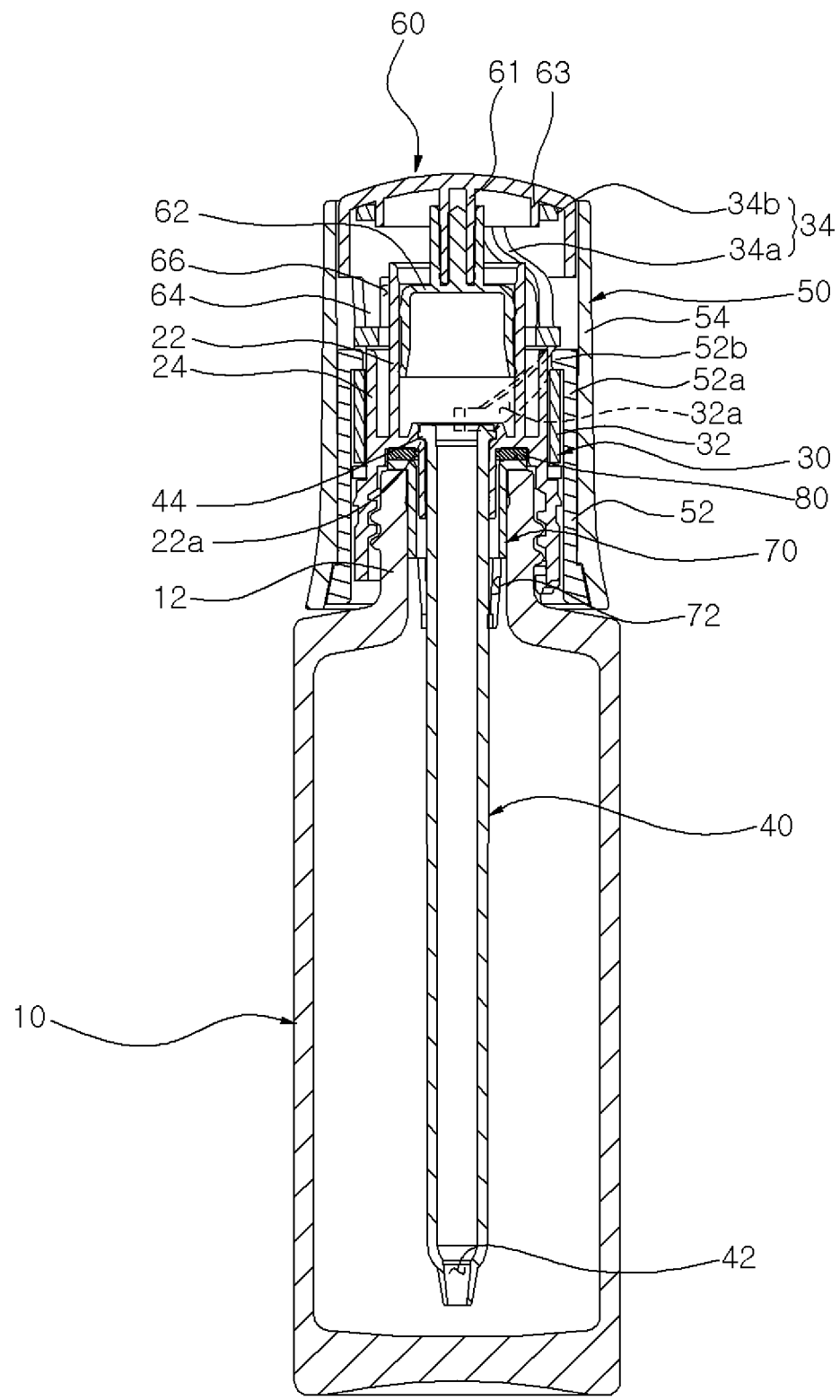
FIG. 3 is a cross-sectional view taken along line A-A of FIG. 1.
Figure 4:
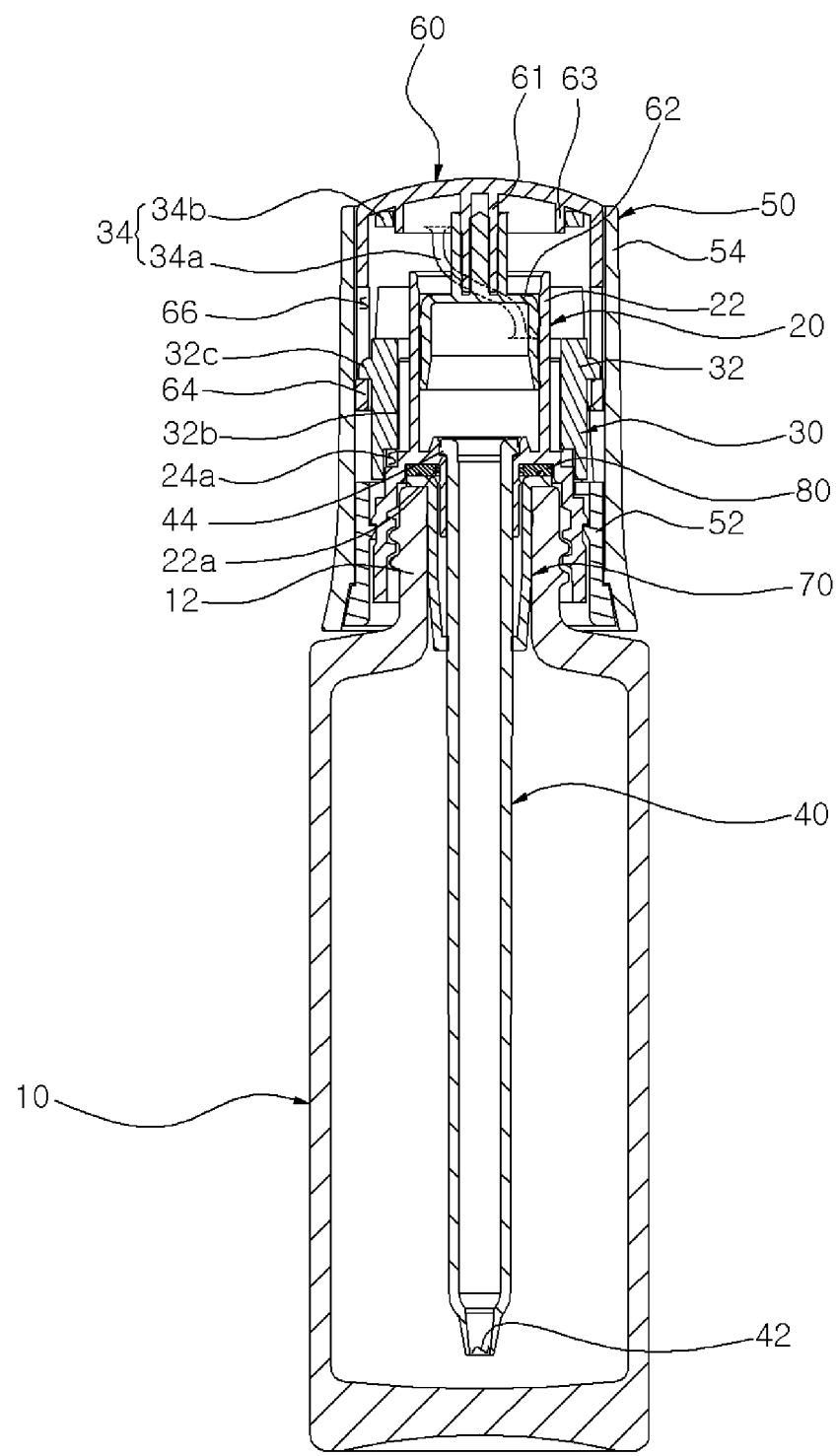
FIG. 4 is a cross-sectional view taken along line B-B of FIG. 1.

FIG. 1 is a perspective view of a cosmetic container according to an embodiment of the present disclosure. FIG. 2 is an exploded perspective view of a cosmetic container according to an embodiment of the present disclosure. FIG. 3 is a cross-sectional view taken along line A-A of FIG. 1. FIG. 4 is a cross-sectional view taken along line B-B of FIG. 1.

As shown, a dropper type cosmetic container according to an embodiment of the present disclosure may include a container body 10, a fixing member 20, an elevating member 30, a dropper tube 40, a rotating member 50, and a push button 60.

The container body 10 is formed in a rigid cylindrical shape and defines the appearance of the cosmetic container. Of course, the shape of the container body 10 is not limited to the rigid cylindrical shape, and the container body 10 may be formed in various shapes or of various materials in consideration of the type or usability or design factors of the contents stored therein. However, because it is necessary to insert the dropper tube 40 having a certain length into the inside of the container body 10, it is appropriate to form the dropper type cosmetic container according to an embodiment of the present disclosure to have a narrow width and a relatively long length.

Liquid or gel cosmetics may be contained in the container body 10. As shown in FIG. 2, an inlet portion 12 may be formed on an upper portion of the container body 10 to fill the cosmetic material through the inlet portion 12, and the dropper tube 40 may be inserted through the inlet portion 12.

A screw thread is formed on an outer periphery of the inlet portion 12 of the container body 10, and a fastening protrusion 16 for preventing rotation of the fixing member 20 protrudes from a lower portion of the screw thread. It is preferable that the fastening protrusions 16 are formed in a pair along the circumference of the inlet portion 12 and disposed opposite to each other.

Meanwhile, a hollow wiper 70 of which the upper and lower portions are opened may be further formed inside the inlet portion 12 of the container body 10. The wiper 70 is in close contact with the outer periphery of the dropper tube 40, and when the dropper tube 40 is separated from the container body 10, the wiper 70 sweeps away the cosmetic material on the outer periphery of the dropper tube 40. At least one cosmetic inflow hole 72 may be formed under the wiper 70 to allow the cosmetic material swept from the dropper tube 60 to flow into the container body 10 again.

The fixing member 20 is formed in a cylindrical shape with opened upper and lower portions, and is fixedly coupled to the container body 10. A screw thread is formed on the lower inner periphery of the fixing member 20 to be screwed with a screw thread formed on the outer periphery of the inlet portion 12 of the container body 10. In the dropper type cosmetic container according to an embodiment of the present disclosure, the container body 10 and the fixing member 20 are shown to be screwed together, but the embodiment is not limited thereto. As long as the container body 10 and the fixing member 20 are stably fixed coupled without spinning with no traction, the container body 10 and the fixing member 20 may be coupled in various coupling schemes such as a coupling of a protrusion and a groove, a force-fitting coupling, or an undercut coupling, and the like.

A cylinder 22 may be formed in the upper center of the fixing member 20 such that the piston 62 of the push button 60 is inserted into the inner space of the cylinder 22. The outer wall 24 may be formed to extend upwardly while spaced apart from the outside of the cylinder 22 by a predetermined interval. In this case, a vertical guide hole 24a for guiding the linear movement of the elevating member 30 may be formed in the outer wall 24. Preferably, the vertical guide hole 24a is formed to be elongated in the elevating and descending directions of the elevating member 30.

In addition, a fastening groove 26 is formed in the lower portion of the fixing member 20 to be coupled to the fastening protrusion 16 of the container body 10. Thus, when the rotating member 50 is rotated, the fixing member 20 may be stably fixed to the container body 10 without spinning. As shown in FIG. 2, the fastening groove 26 may include an insertion groove 26a that extends upward from the lower end of the fixing member 20 and into which the fastening protrusion 16 is inserted, and an elastic groove 26b that extends from the insertion groove 26a to a side and allows a portion of a lower end of the fixing member 20 to elastically move. In this case, a pair of fastening grooves 26 are preferably formed at the lower end of the fixing member 20 so as to correspond to the fastening protrusion 16 of the container body 10, and disposed opposite to each other.

That is, when the container body 10 and the fixing member 20 are screw-coupled to each other, the fixing member 20 is gradually lowered so that the end is adjacent to the fastening protrusion 16 of the container body 10. The fastening protrusion 16 is rotated while forcibly pushing up the end of the fixing member 20 located under the elastic groove 26b, and is momentarily inserted into the insertion groove 26a. At the same time, the end of the fixing member 20 located under the elastic groove 26b is elastically restored. Accordingly, the user may stably fasten the container body 10 and the fixing member 20 without exerting a large force.

Meanwhile, as shown in FIG. 3, a ring-shaped sealing ring 80 may be further formed on the inner lower surface of the fixing member 20. The sealing ring 80 further improves the sealing force inside the container body 10 while pressing the upper end of the wiper 70 when the container body 10 and the fixing member 20 are coupled. In this case, the sealing ring 80 may be formed of an elastic material. In particular, preferably, the sealing ring 80 may be formed of at least one of urethane rubber, natural rubber, elastomer, nitrile-butadiene rubber (NBR), silicone, or formed of acrylonitrile butadiene styrene (ABS), thermo plastic elastomer (TPE), or elastic polypropylene or polyethylene.

The elevating member 30 is coupled to the upper portion of the fixing member 20, and moves up or down in a straight line from the fixing member 20.

The elevating member 30 may include an elevating body 32 surrounding the upper outside of the fixing member 20, and an elastic body 34 formed on one side of the elevating body 32 to elastically support the push button 60.

The elevating body 32, which enables the elevating member 30 to move up or down, may be coupled while surrounding the outer wall 24 of the fixing member 20. As shown in FIG. 2, there is formed an elevating guide hole 32a for guiding the elevation of the elevating member 30 on the side of the elevating body 32. The elevating guide hole 32a is coupled to an e elevating protrusion 52b of the rotating member 50. The elevating guide hole 32a may be formed in a spiral shape inclined in one direction along the circumference of the elevating body 32. A vertical guide protrusion 32b for guiding the linear movement of the elevating member 30 may protrude from the inner periphery of the elevating body 32. The vertical guide protrusion 32b may be coupled to the vertical guide hole 24a of the fixing member 20 and, like the vertical guide hole 24a, may be elongated in the elevating and descending directions of the elevating member 30. In addition, a movement limiting protrusion 32c may protrude from the outer periphery of the elevating body 32 to prevent separation of the push button 60 and limit the movement section. In this case, it is preferable that the elevating guide hole 32a, the vertical guide protrusion 32b, and the movement limiting protrusion 32c are all formed in a pair for smooth operation and stable fixation between the respective parts and disposed opposite to each other.

The elastic body 34 extends from the end of the elevating body 32 to elastically support the push button 60. The elastic body 34 may include an elastic support portion 34a that is gently bent in one direction from the elevating body 32, and a support portion 34b that is in close contact with the inner surface of the push button 60 to support the push button 60 while being supported by the elastic support part 34a.

Meanwhile, the elastic body 34 may be formed of a synthetic resin material. Preferably, the elastic body 34 may be formed of a thermosetting resin or a thermoplastic resin, where the thermosetting resin includes at least one of an epoxy resin, an amino resin, a phenol resin, and a polyester resin, and the thermoplastic resin includes at least one of polyethylene, acrylic, polypropylene, polystyrene, polyvinyl chloride, Teflon, nylon, and polyacetal resins. In particular, the elastic body 34 is most preferable to be formed of polyethylene. Of course, the elastic body 34 is not limited to the above-described materials, and may be formed of various materials as long as the material has certain elasticity.

In this case, it is preferable that the elastic body 34 is injection-molded integrally with the elevating body 32, or double injection or insert injection molded.

That is, in a conventional dropper container, the elastic member that provides elasticity to the button is made of a metallic spring, so that the elastic member formed of the metallic spring must be separated from other parts and disposed, so recycling is not easy. Accordingly, in the present disclosure, the elastic body 34 for elastically supporting the push button 60 is formed of a synthetic resin material in the same manner as other parts, so that the elasticity and repulsion force are not lowered compared to the conventional metallic elastic body, and the elastic body 34 may be easily separated and collected or recycling may be easy.

The dropper tube 40 is fixedly coupled with the fixing member 20 to suck and discharge the cosmetic material contained in the container body 10. As shown in FIG. 3, one side of the dropper pipe 40 is formed with a suction and discharge port 42 serving as a suction or discharge hole of the cosmetic material, the opposite side is connected to the inside of the cylinder 22 of the fixing member 20. In addition, a seating protrusion 44 may be formed on the outer periphery of the upper end of the dropper pipe 40 to be fixedly coupled while being placed on a seating protrusion 22a formed inside the cylinder 22.

The dropper tube 40 may be formed of a glass material so that the inside can be seen, but is not limited thereto, and in consideration of the type, usability, durability, and design factors of a cosmetic material that is sucked into the inside, the dropper tube may be formed variously.

The rotating member 50 is rotatably coupled to the fixing member 20, surrounds the outsides of the fixing member 20 and the elevating member 30, and includes a rotation inner cap 52 and a rotation outer cap 54 which are fixedly coupled to each other.

As shown in FIG. 2, the rotation inner cap 52 of the rotating member 50 may have an upper extension portion 52a extending upward, and an elevating protrusion 52b may protrude inwardly from the inner periphery of the upper extension portion 52a to be coupled to the elevating guide hole 32a of the elevating member 30. In addition, a fitting groove 52c may be formed on the lower outer periphery of the rotation inner cap 52 so that the rotation outer cap 54 does not spin with no traction with respect to the rotation inner cap 52, and a first fastening protrusion 52d, which fixes the rotation outer cap 54 to prevent the outer cap 54 from being separated upward from the rotation inner cap 52, may be formed on an upper portion adjacent to the fitting groove 52c. In this case, the upper extension portion 52a, the elevating protrusion 52b, the fitting groove 52c and the first fastening protrusion 52d are all formed in a pair for smooth operation and stable fixation between respective parts and disposed opposite to each other.

The rotation outer cap 54 of the rotating member 50 surrounds and protects the outer sides of the fixing member 20, the elevating member 30 and the push button 60 as well as the rotation inner cap 52. A fitting protrusion 54a may be formed on the lower inner periphery of the rotation outer cap 54 and coupled to the fitting groove 52c of the rotation inner cap 52, and a second fastening protrusion 54b may be formed on an upper portion adjacent to the fitting protrusion 54a to be undercut coupled to the first fastening protrusion 52d of the rotation inner cap 52. Accordingly, the rotation outer cap 54 does not spin to the rotation inner cap 52 with no traction and is not separated upward from the rotation inner cap 52.

The push button 60 serves to discharge the cosmetic material sucked into the dropper tube 40 to the outside while being pressed or restored, or to suck the cosmetic material contained in the container body 10 into the dropper tube 40, and is inserted into the inside or protrudes outwardly of the rotating member 50 while rising and descending together with the elevating member 30.

As shown in FIG. 3, a first lower extension protrusion wheel 61 may be formed at the inner center of the push button 60, and the piston 62 may be fixedly coupled to the first lower extension protrusion wheel 61. The piston 62 is inserted into the cylinder 22 of the fixing member 20, and the outer surface is reciprocated within a certain section while being in close contact with the inner surface of the cylinder 22, so that the inner volume of the cylinder 22 is changed. Thus, the cosmetic material is sucked or discharged through the dropper pipe 40 connected to the inner space of the cylinder 22.

Meanwhile, the piston 62 may be formed of a soft material. Preferably, the piston 62 may be formed of one of urethane rubber, natural rubber, elastomer, nitrile-butadiene rubber (NBR) and silicone, or one of polypropylene, polyethylene, acrylonitrile butadiene styrene (ABS) and thermo plastic elastomer (TPE) having elasticity. In particular, the piston 62 may be formed of nitrile-butadiene rubber (NBR). Of course, the piston 62 is not limited to the above-described materials, and may be formed of various materials as long as the materials have certain elasticity.

In addition, a second lower extension protrusion wheel 63 is formed while being spaced apart from the outside of the first lower extension protrusion wheel 61 of the push button 60 by a predetermined interval. The end of the elevating member 30, that is, the support portion 34b of the elastic body 34 is fitted to the outside of the second lower extension protrusion wheel 63 so that the elastic body 34 is fixed at a certain position without shaking sideways.

As shown in FIG. 4, a protrusion 64 may extend downward from the outer wall of the push button 60 to surround a portion of the outer periphery of the elevating member 30, and a movement limiting hole 66 may be formed on the protrusion 64 to be elongated in the operation direction of the push button 60 such that the movement limiting protrusion 32c of the elevating member 30 may be inserted in the movement limiting hole 66. Accordingly, the moving section of the push button 60 and the compression range of the elastic body 34 are limited. Of course, by changing the length of the movement limiting hole 66 to change the movement range of the movement limiting protrusion 32c fitted into the movement limiting hole 66, the moving section of the push button 60 may also be freely adjusted.

That is, in the related art, while the button protruding to the outside of a cap is pressed to the end, the synthetic resin elastic member is excessively compressed by the button, and thus the synthetic resin elastic member is damaged or easily deformed when repeatedly used, so that the operation of discharging cosmetics is not performed smoothly. Therefore, according to a dropper type cosmetic container of an embodiment, the compression range of the synthetic resin elastic body 34 that elastically supports the push button 60 may be constantly adjusted by restricting the movement section of the push button 60 through the configuration of the movement limiting protrusion 32c and the movement limiting hole 66, so that it is possible to prevent the detachment of the push button 60 and prevent damage and deformation due to excessive compression of the synthetic resin elastic body 34. As the restoring force of the synthetic resin material elastic body 34 is always properly maintained, even if the dropper type cosmetic container is repeatedly used, a cosmetic discharge operation may be performed smoothly.

In addition, in the related art, when the button is inserted into the cap, the synthetic resin elastic member is contained in the cap in a compressed state, so that the restoring force is lowered due to its material properties when used for a long period of time. Accordingly, according to the present disclosure, the elevating member 30 including the elastic body 34 and the push button 60 including the piston 62 may move up or down together when the rotating member 50 rotates, so that the elastic body 34 is always maintained in an uncompressed state, thereby preventing the restoring force of the synthetic resin elastic body 34 from deteriorating.

Figure 5:
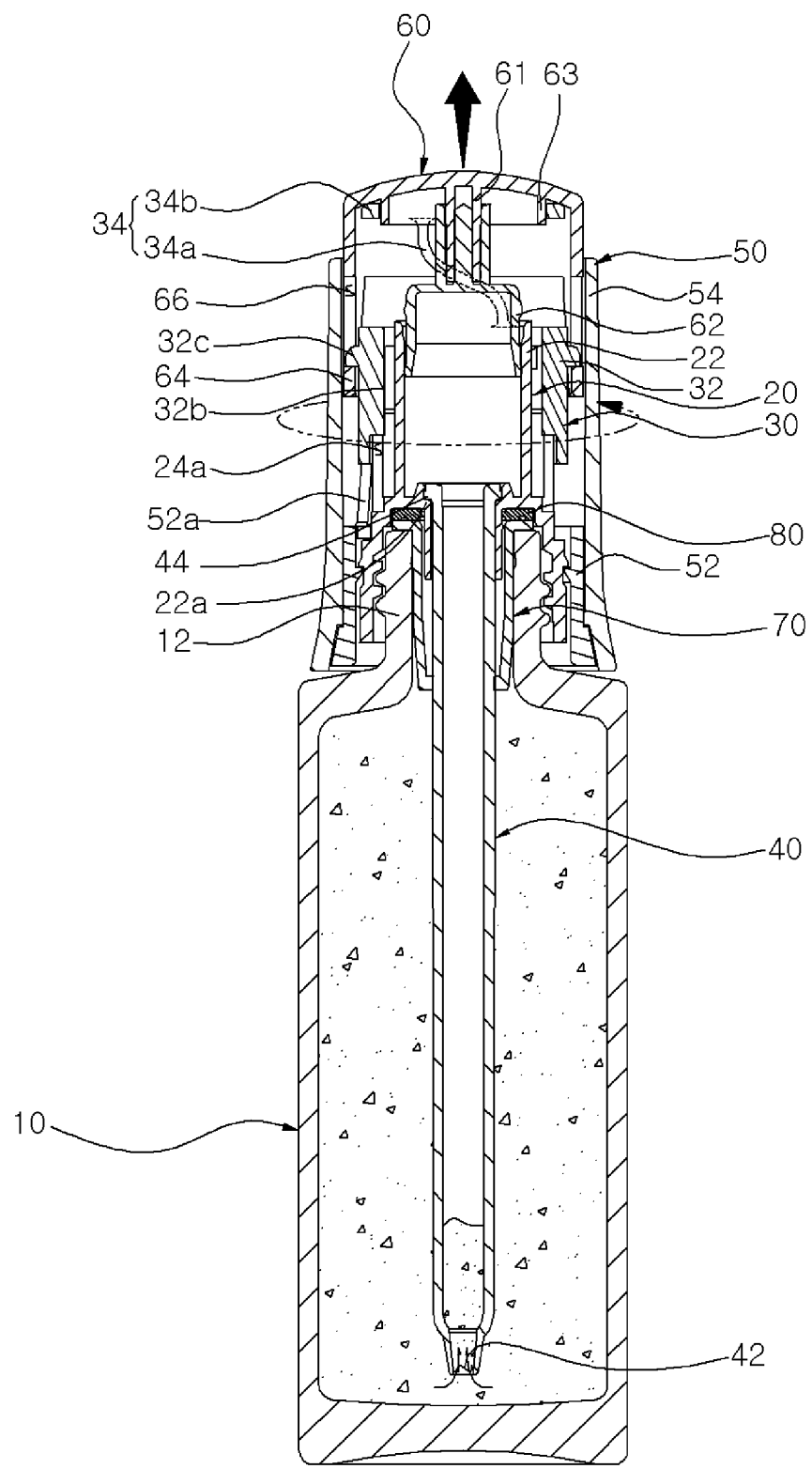
FIG. 5 is a cross-sectional view taken along line B-B of FIG. 1, which illustrates a state in which a push button appears to the outside by rotating the rotating member and at the same time, a cosmetic material is sucked into the dropper tube, according to an embodiment of the present disclosure.
Figure 6:
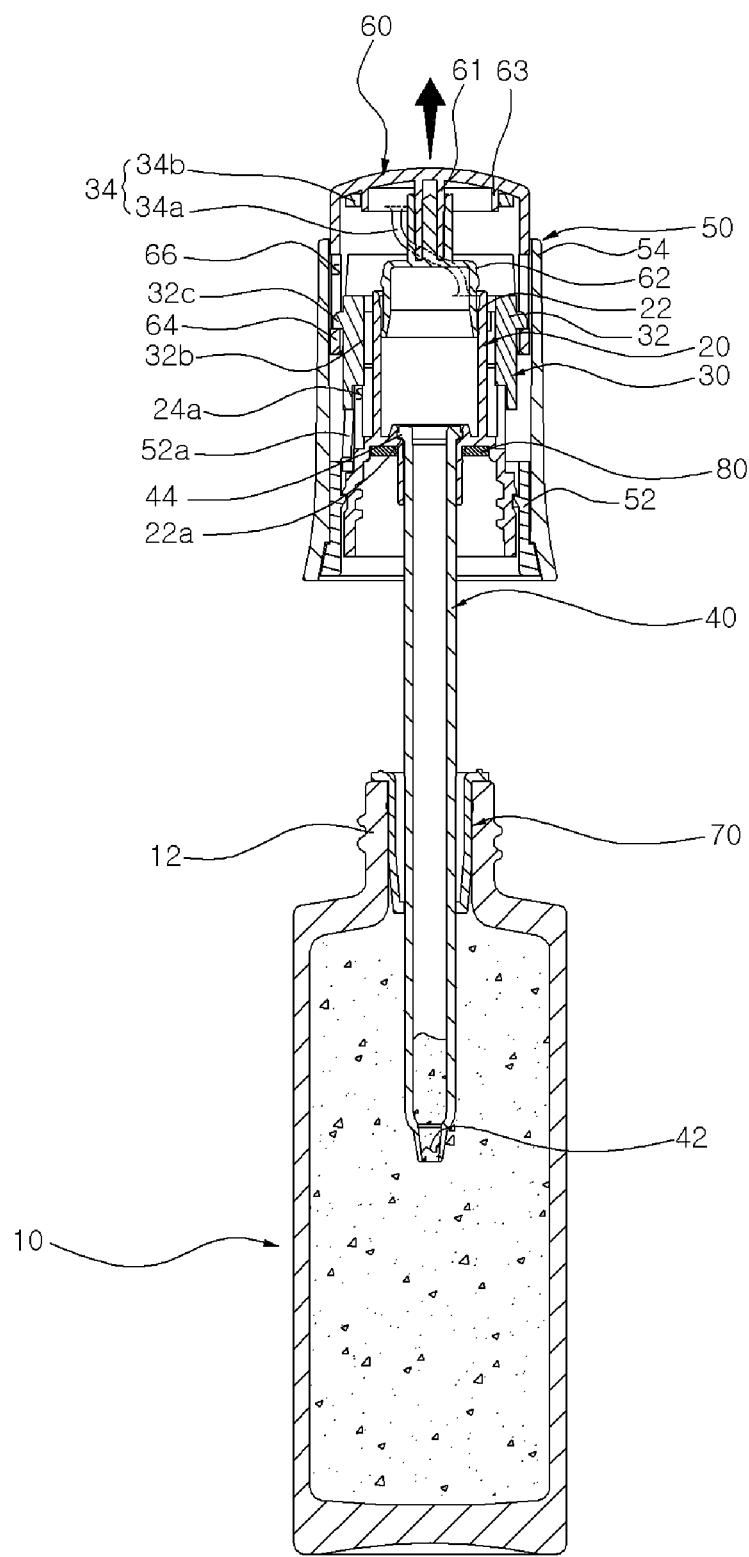
FIG. 6 is a cross-sectional view taken along line B-B, which illustrates a state of separating the fixing member from the container body according to an embodiment of the present disclosure.
Figure 7:
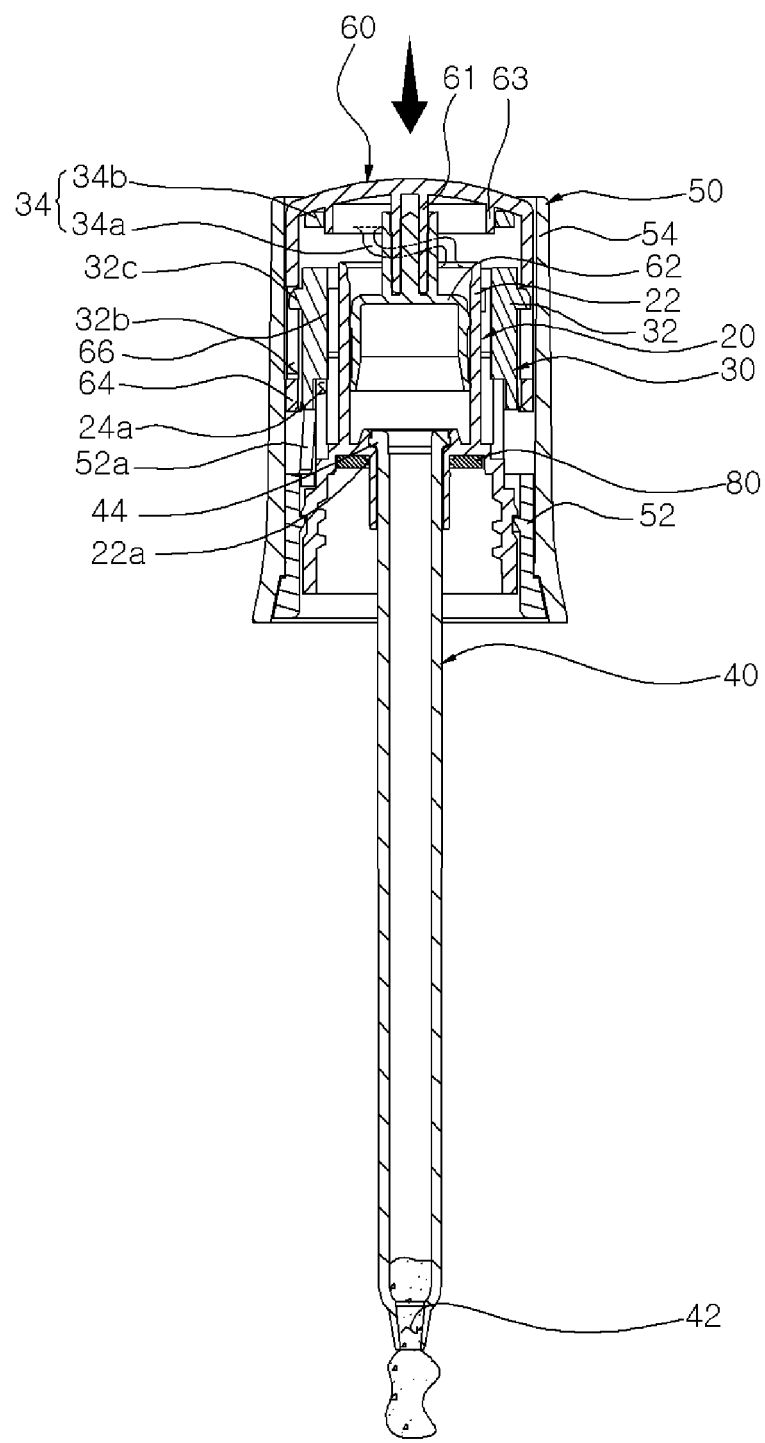
FIG. 7 is a cross-sectional view taken along line B-B, which illustrates a state in which a cosmetic material sucked into the dropper tube is discharged to the outside by pressing the push button according to an embodiment of the present disclosure.

FIGS. 5 to 7 are views illustrating the use of a dropper type cosmetic container according to an embodiment of the present disclosure. A method of using a dropper type cosmetic container according to an embodiment of the present disclosure will be described with reference to FIGS. 5 to 7.

FIG. 5 is a cross-sectional view taken along line B-B of FIG. 1, which illustrates a state in which a push button appears to the outside by rotating the rotating member and at the same time, a cosmetic material is sucked into the dropper tube, according to an embodiment of the present disclosure. FIG. 6 is a cross-sectional view taken along line B-B, which illustrates a state of separating the fixing member from the container body according to an embodiment of the present disclosure. FIG. 7 is a cross-sectional view taken along line B-B, which illustrates a state in which a cosmetic material sucked into the dropper tube is discharged to the outside by pressing the push button according to an embodiment of the present disclosure.

In order to use the dropper type cosmetic container according to the present disclosure, as shown in FIG. 5, the outer cap 54 is rotated with one hand in a counterclockwise direction while the container body 10 is held with the other hand, the container body 10 is opened.

When the rotation outer cap 54 is rotated in a counterclockwise direction, while the rotation inner cap 52 fixedly coupled to the inside of the rotation outer cap 54 rotates together, the elevating protrusion 52b formed on the rotation inner cap 52 moves within the elevating guide hole 32a of the elevating member 30. In this case, the vertical guide projection 32b formed on the inner periphery of the elevating member 30 is fitted into the vertical guide hole 24a of the fixing member 20 fixedly coupled to the container body 10, so that the elevating member 30 is not rotated, and accordingly, the elevating protrusion 52b of the rotation inner cap 52 is horizontally rotated to push the elevating member 30 upward and linearly move the elevating member 30 upward.

At the same time, while the push button 60 elastically supported by the elastic body 34 of the elevating member 30 and the piston 62 located in the cylinder 22 while being coupled to a lower portion of the push button 60 move vertically together, the push button 60 protrudes upward of the rotation outer cap 54.

When the elevating member 30, the push button 60 and the piston 62 are completely raised, the elevating protrusion 52b of the rotating inner cap 52 forcibly rotates the fixing member 20 to release the screw coupling between the container body 10 and the fixing member 20.

Thereafter, as shown in FIG. 6, while separating the fixing member 20, the elevating member 30, the rotating member 50 and the push button 60 from the container body 10, the dropper tube 40 is taken out from the container body 10.

Then, as shown in FIG. 7, when the dropper tube 40 is placed onto the skin and the push button 60 is pressed, while the piston 62 coupled to the lower portion of the push button 60 moves downwardly in the cylinder 22, the air inside the cylinder 22 is pushed out, so that the cosmetic material sucked into the dropper tube 40 is discharged to the outside through the suction and discharge port 42. In this case, the movement limiting protrusion 32c formed on the elevating member 30 is fitted into the movement limiting hole 66 formed in the push button 60, so that the movement section of the push button 60 is limited by the length of the movement limiting hole 66, and the compression range of the synthetic resin elastic body 34 is constantly adjusted while the synthetic resin elastic body 34 is not excessively compressed.

After the make-up is finished, the container body 10 is closed while inserting the dropper tube 40 into the inlet portion 12 of the container body 10, and the container body 10 and the fixing member 20 are screw coupled to each other by rotating the rotational cap 54 in a clockwise direction.

When the rotational cap 54 is continuously rotated in a clockwise direction, while the rotation inner cap 52 fixedly coupled to the inside of the rotation outer cap 54 rotates together, the elevating protrusion 52b formed on the rotation inner cap 52 moves within the elevating guide hole 32a of the elevating member 30. In this case, the vertical guide protrusion 32b formed on the inner periphery of the elevating member 30 is fitted into the vertical guide hole 24a of the fixing member 20 fixedly coupled to the container body 10, so that the elevating member 30 Is not rotated, and accordingly, the elevating protrusion 52b of the rotation inner cap 52 is horizontally rotated, and the elevating member 30 is pulled down and linearly moved downward.

At the same time, while the movement limiting protrusion 32c of the elevating member 30 pulls down one side end of the movement limiting hole 66 of the push button 60, the push button 60 and the piston 62 coupled to the lower portion of the push button 60 is linearly moved downward, so that the push button 60 is inserted into the inside of the rotation outer cap 54, and the air inside the dropper tube 40 is discharged through the suction and discharge port 42. In this case, the elastic body 34 of the elevating member 30 is moved and stored in the inside of the rotation outer cap 54 while maintaining the non-compressed state.

While the present disclosure has been described above using particular examples, including specific elements, by way of limited embodiments and drawings, it is to be appreciated that these are provided merely to aid the overall understanding of the present disclosure, the present disclosure is not to be limited to the embodiments above, and various modifications and alterations can be made from the disclosures above by a person having ordinary skill in the art to which the present disclosure pertains. Therefore, the spirit of the present disclosure must not be limited to the embodiments described herein, and the scope of the present disclosure must be regarded as encompassing not only the claims set forth below, but also their equivalents and variations.

What is claimed is:

1. A dropper type cosmetic container comprising:
   a container body for containing a cosmetic material therein;
   a fixing member fixedly coupled to the container body and formed with a cylinder;
   an elevating member coupled to the fixing member to move up or down and formed with a synthetic resin elastic body;
   a dropper tube connected to the fixing member to suck and discharge the cosmetic material contained in the container body;
   a rotating member rotatably coupled to the fixing member; and
   a push button moving up or down together with the elevating member and having one side coupled to a piston,
   wherein a movement limiting protrusion is formed on one side of the elevating member, and a movement limiting hole is formed in one side of the push button, so that the movement limiting protrusion is coupled to the movement limiting hole, thereby limiting a movement section of the push button and a compression range of the elastic body.

2. The dropper type cosmetic container of claim 1, wherein the container body is formed with an inlet portion, and the inlet portion is formed with a wiper which is in close contact with an outer periphery of the dropper tube.

3. The dropper type cosmetic container of claim 1, wherein the fixing member is formed with a vertical guide hole, and the elevating member is formed on an inner periphery thereof with a vertical guide protrusion so that the vertical guide protrusion is coupled to the vertical guide hole.

4. The dropper type cosmetic container of claim 1, wherein the dropper tube has one side formed with a suction/discharge port and an opposite side connected to an inside of the cylinder of the fixing member.

5. The dropper type cosmetic container of claim 1, wherein the elevating member includes an elevating body surrounding an upper outer side of the fixing member and an elastic body formed on one side of the elevating body to elastically support the push button.

6. The dropper type cosmetic container of claim 5, wherein the elevating body and the elastic body of the elevating member are integrally injection-molded.

7. The dropper type cosmetic container of claim 1, wherein the rotating member includes a rotation inner cap and a rotation outer cap, and the rotation inner cap and the rotation outer cap are formed with a fitting protrusion and a fitting groove, respectively, so that the rotation inner cap and the rotation outer cap are coupled to each other.

8. The dropper type cosmetic container of claim 1, wherein the rotating member and the elevating member are formed with an elevating protrusion and an elevating guide hole, respectively, so that the rotating member and the elevating member are coupled to each other.

9. The dropper type cosmetic container of claim 1, wherein the push button has a protrusion extending to one side to surround an outer periphery of the elevating member, and the protrusion is formed with a movement limiting hole that extends linearly.

10. The dropper type cosmetic container of claim 1, wherein the elevating member including the elastic body and the push button including the piston move up or down together as a single module when the rotating member rotates, and the elastic body is always maintained in an uncompressed state.

* * * * *